United States Patent [19]
Lindquist et al.

[11] Patent Number: 6,066,121
[45] Date of Patent: May 23, 2000

[54] DISPOSABLE LIQUID-ABSORBENT ARTICLE HAVING LONGITUDINAL LIQUID BARRIER MEANS, METHOD AND APPARATUS FOR ITS MANUFACTURE

[75] Inventors: Bengt Lindquist, Lerum, Sweden; Clas Olsen, Vestskogen, Norway

[73] Assignee: SCA Hygiene Products AB, Goteberg, Sweden

[21] Appl. No.: 08/737,480

[22] PCT Filed: May 15, 1995

[86] PCT No.: PCT/SE95/00539

§ 371 Date: Jan. 23, 1997

§ 102(e) Date: Jan. 23, 1997

[87] PCT Pub. No.: WO95/31163

PCT Pub. Date: Nov. 23, 1995

[30] Foreign Application Priority Data

May 16, 1994 [SE] Sweden .................................. 9401681

[51] Int. Cl.[7] .............................. A61F 13/15; A61F 13/20
[52] U.S. Cl. .................................. 604/385.2; 604/385.1; 604/378; 604/365; 604/369; 28/121
[58] Field of Search ..................... 604/365, 369, 604/358, 373, 385.1, 385.2, 387; 28/118–121

[56] References Cited

U.S. PATENT DOCUMENTS

| | | |
|---|---|---|
| 3,860,003 | 1/1975 | Buell . |
| 4,050,462 | 9/1977 | Woon et al. . |
| 4,636,207 | 1/1987 | Buell ....................................... 604/370 |
| 4,801,345 | 1/1989 | Dussaud et al. . |
| 4,900,384 | 2/1990 | Sanders et al. ......................... 156/204 |
| 5,114,420 | 5/1992 | Igaue et al. . |
| 5,167,653 | 12/1992 | Igaue et al. ............................ 604/385.2 |
| 5,246,432 | 9/1993 | Suzuki et al. .......................... 604/385.2 |
| 5,275,590 | 1/1994 | Huffman et al. ....................... 604/385.2 |
| 5,399,176 | 3/1995 | Chen ...................................... 604/385.1 |
| 5,476,458 | 12/1995 | Glaug et al. ............................ 604/378 |
| 5,599,334 | 2/1997 | Johnston et al. ........................ 604/387 |
| 5,843,067 | 12/1998 | Trombetta et al. ..................... 604/387 |

FOREIGN PATENT DOCUMENTS

| | | |
|---|---|---|
| 563841 | 9/1984 | Australia . |
| 0 219 326 A2 | 4/1987 | European Pat. Off. . |
| 0 219 326 B1 | 4/1987 | European Pat. Off. . |
| 0 337 969A1 | 10/1989 | European Pat. Off. . |
| 0 534 488 A1 | 3/1993 | European Pat. Off. ............... 604/387 |
| 2 234 157 | 1/1991 | United Kingdom . |
| WO 88/00010 | 1/1988 | WIPO . |
| WO 92/07536 | 5/1992 | WIPO . |
| WO 93/12745 | 7/1993 | WIPO . |

*Primary Examiner*—Mickey Yu
*Assistant Examiner*—Tram A. Nguyen
*Attorney, Agent, or Firm*—Burns, Doane, Swecker & Mathis, L.L.P.

[57] ABSTRACT

A liquid-absorbent article to be worn by a user and comprising a substantially longitudinal absorption body (1) and a cover (2) enclosing the same. On a first side, facing the user in an in-use position, the cover displays a liquid pervious first cover-sheet (3) and on a second side, facing away from the user in an in-use position, the cover displays a second cover-sheet (4). On said first side is provided longitudinal liquid barrier means (17, 18) folded into tunnel shape, forming a channel (17', 18') with a longitudinal tunnel wall (17", 18"). Said folded portions enclose longitudinal means (24, 25) with an elastically resilient supporting action acting in all directions transverse to the longitudinal direction of the article against the tunnel wall (17", 18") of the folded portion.

12 Claims, 4 Drawing Sheets

FIG. 8
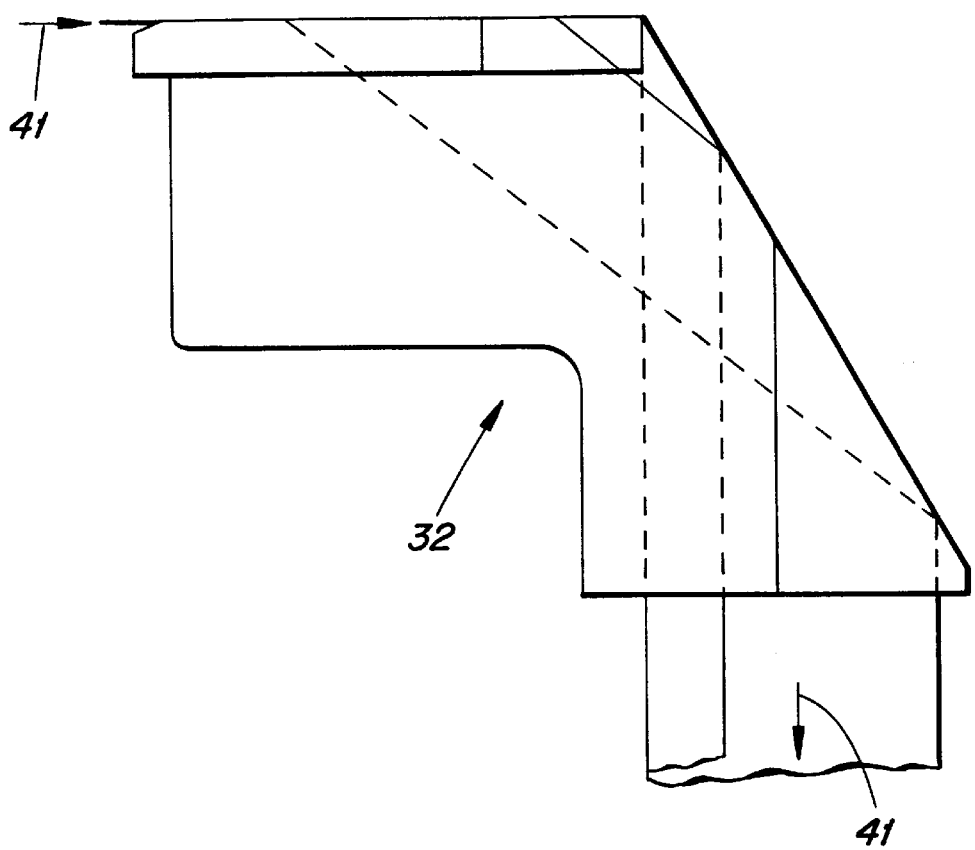
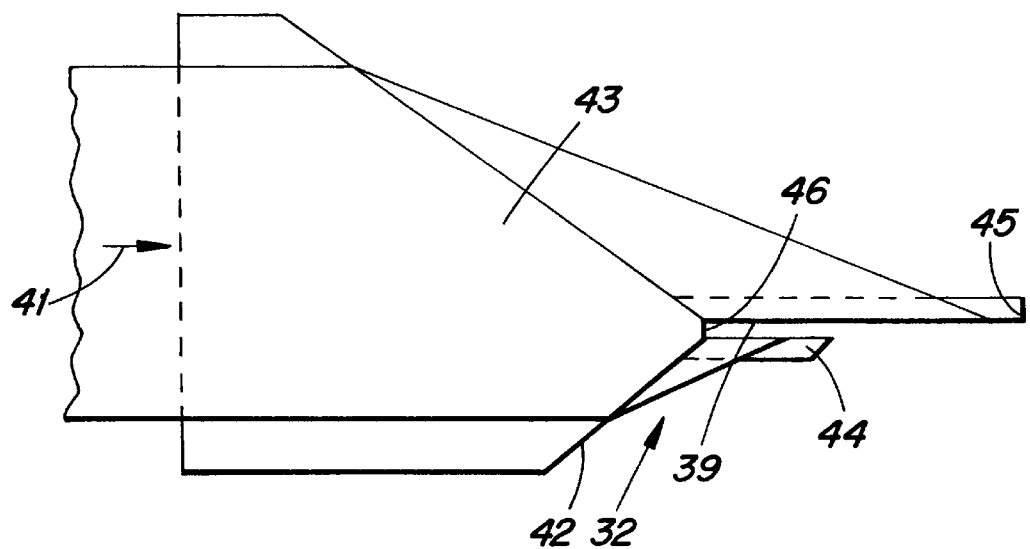
FIG. 9

DISPOSABLE LIQUID-ABSORBENT ARTICLE HAVING LONGITUDINAL LIQUID BARRIER MEANS, METHOD AND APPARATUS FOR ITS MANUFACTURE

CROSS REFERENCES TO RELATED APPLICATIONS

This application claims priority under 35 U.S.C. §§119 and/or 365 to Swedish Patent Application No. 9401681-3 filed on May 16, 1994 and PCT International Application No. PCT/SE95/00539 filed on May 15, 1995.

TECHNICAL FIELD

The present invention relates to a liquid-absorbent article.

The present invention also relates to a method and an apparatus for the manufacture of a liquid-absorbent article.

The present invention more particularly relates to articles provided with leakage barriers primarily intended for use on sanitary towels, but that of course may be used on other types of absorbent articles such as incontinence protection, diapers or similar.

Edge-leakage is a widespread problem primarily on sanitary towels, since patches of menstrual blood are difficult to remove and are experienced as extremely embarrassing by the affected user. Sanitary towels, in contrast to diapers or the like, are fastened directly in the panties by the user herself. Since both the size and shape of ladies panties vary greatly, it may easily happen that the positioning of the sanitary towel is less than optimal and varies from one time to another and between different users. An additional factor that increases the risk of leakage is that the sanitary towel is deformed during use, or moves away from its original position in the panties. The negative effect of erroneous positioning or deformation of the sanitary towel may to a certain extent be alleviated by the provision of raised edge-leakage barriers on each side of the longitudinal side-edges of the sanitary towel. Even if, by accident, the sanitary towel has assumed such a position that it will be wetted near an edge-portion, the liquid may thereby be prevented from pouring out over the edge and giving rise to soiling of the user's clothes.

Edge-leakage barriers are furthermore effective for controlling the spreading of liquid in the longitudinal direction of the sanitary towel. This is particularly useful in conjunction with the nowadays commonly available, extremely thin sanitary towels which often have an absorption core with high liquid-spreading capacity. The drawback with such absorption cores, is that they usually spread out liquid equally well in all directions. Hereby, leakage arises as soon as the liquid reaches out to the side-edges of the sanitary towel.

BACKGROUND OF THE INVENTION

A number of different raised edge-leakage barriers are known in the prior art, see for example WO93/12795, showing edge-leakage barriers on a sanitary towel, which are formed by folded portions of the cover of the sanitary towel. An elastic cord, fastened and prestressed at each end, extends along the inside of the formed folds and keeps the barrier raised in an in-use position. Ensuring a safe fastening of the ends of the cord means placing great demands upon the manufacture of the sanitary towels. Furthermore, the cord does not counteract sideways flattening. Additionally, transversal folds are formed by the action of the elastic cord in the barrier-wall, which may be experienced as uncomfortable by the user.

An additional problem with modern sanitary towels, are that the surface material often consists of a perforated plastic layer, having favourable characteristics in terms of high liquid-permeability, high surface dryness and little rewetting (i.e. small risk that liquid is pressed back out again through the layer). Such a material is experienced as "plasticky" by many users and therefore it has become common to provide the edge-portions of the sanitary towels with more "textile" strips of non-woven material (fibre cloth). An example of a document describing such "textile edges" is SE-B-900349D-1, which shows edge-portions with flat folds, yielding a very limited liquid-stopping effect.

SUMMARY OF THE INVENTION

The object with the present invention is to provide a liquid-absorbent article with an edge-leakage barrier, which by means of an integrated resilient action effectively counteracts squeeze in a direction of height as well as in a sideways direction.

Said object is achieved by a liquid-absorbent article according to the present invention.

Said object is also achieved by a method and an apparatus for the manufacture of a liquid-absorbent article.

BRIEF DESCRIPTION OF THE DRAWINGS

The invention will in the following be described in greater detail with a couple of embodiments with reference to the appended drawings, in which FIGS. 8 and 9 shows the fold-over device in a sideview and a topview respectively.

DESCRIPTION OF PREFERRED EMBODIMENTS

Figure 1:
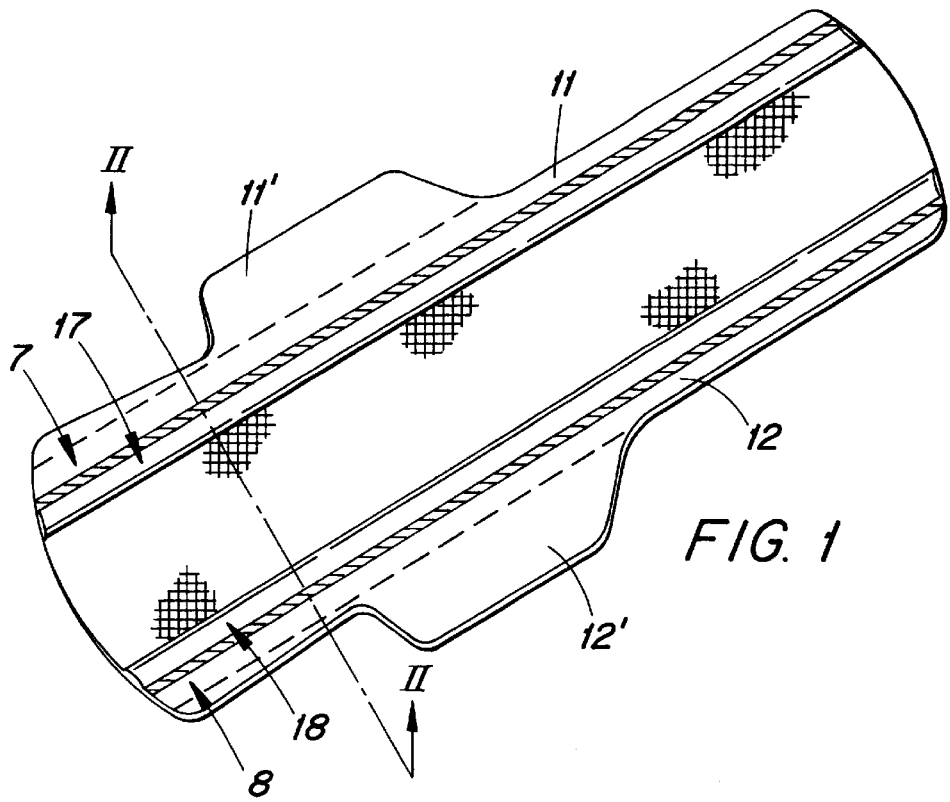
FIG. 1 is a perspective view of a liquid-absorbent article according to the invention in the shape of a sanitary towel.
Figure 2:
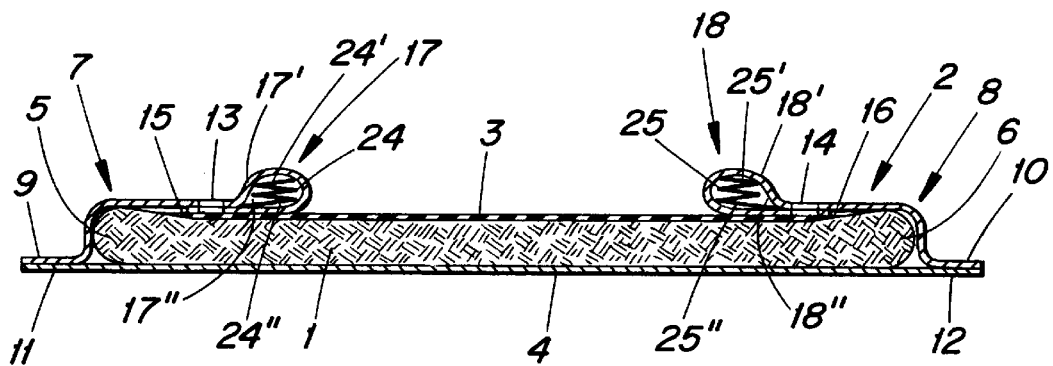
FIG. 2 is a cross-section along the line II—II in FIG. 1, showing the edge-barriers with elastic means in a first embodiment.

The sanitary towel shown in FIG. 1 and 2 generally comprises a substantially longitudinal absorption-body for liquids and a cover 2 enclosing the same. In the shown embodiment, the cover is provided with a liquid-pervious cover-sheet 3, which in an in-use position is facing the user. The liquid-pervious sheet 3 suitably consists of a non-absorbent cloth or a perforated plastic film. The cover is also provided with a preferably liquid-proof cover-sheet 4, for example made of plastic film or a hydrophobed fibre cloth, said cover-sheet 4 facing away from the user in an in-use position. In the shown embodiment, the liquid-pervious cover-sheet 3 extends over the central portion of the sanitary towel, over its entire length, but not over its width, while the liquid-proof cover-sheet 4 extends outside of the longitudinal edges 5, 6 of the absorption body 1. In the shown embodiment, the cover is enclosed by two edge-strips 7, 8 of a skin-friendly "textile" material of for example fibre cloth (non-woven) of a polymer, which along an outer edge-portion 9, 10 are joined with the liquid-proof sheet forming flange-like longitudinal edge-portions 11, 12 of the sanitary towel. In the shown embodiment, the longitudinal edge-portions are each provided with a wing-like projection 11', 12', which by adhesive glue after folding over an edge of the panties may be fastened for fixing the sanitary towel. The joining between the different sheets in the cover 2 is for example achieved by heating the material to a melting temperature, for instance by ultra-sound. In a similar fashion, the inner edge-portions 13, 14 of the edge-strips 7, 8 are joined with the longitudinal edge-portions 15, 16 of the liquid-pervious cover-sheet 3. Instead of welding, i.e. melting the sheets together, gluing may of course be used. Furthermore, the cover-sheet 3 may alternatively extend completely under the edge-strips 7, 8 and be directly joined to the second cover-sheet 4.

In order to form longitudinal edge-leakage barriers 17, 18, the edge-strips 7, 8 are folded-over in order to form a fully closed tunnel-shape enclosing a channel 17", 18", whereby the inner edge-portions 13, 14 are inserted between the liquid-pervious sheet 3 and the underside of the edge-strips and are also joined to the same, for example by gluing or welding through the application of heat or ultrasound. The tunnel shape may alternatively be formed solely by the cover-sheet 3 or by said sheet and the edge-strips 7, 8, which for example may be folded into an omega-shape with the sheet 3 as a base-sheet. According to the invention, the folded-over edge-strips 7, 8 are provided with elastic means or fill-in materials which in the embodiment shown in FIG. 2 comprise a strip 24, 25 folded into a bellows-shape in cross-secton, and made for example of fibre cloth (non-woven) holding the edge-barriers in an upright position and counteracting squeeze in a direction of height as well as in a sideways direction.

According to the embodiment in FIG. 2, a combination of textile edges and raised edge-leakage barriers has been achieved. The main component is the folded material inside the outer channels. The folded material should be of a type having a certain built-in elastically resilient supporting action in order to provide elastic support to the formed tunnel wall 17', 18'. Furthermore, the material should be substantially insensitive to wetting so that it maintains its characteristics during use. The material hitherto tested is a thermobound non-woven material of polypropylene fibres. Whilst other types of fibres with relatively high built-in resilient action are of course applicable, as are materials that have been treated (for example with a coating) so as to increase the resilient action. Each strip 24, 25 is thus provided with one or more longitudinal folds having a V- or Z-(zigzag) shaped cross-section with a built-in pre-stress transverse the longitudinal direction of the strips. The strips are fastened at their edge-portions 24', 24", 25', 25" at least partially abutting the tunnel walls 17', 18'. In the shown embodiment, the folded strips 24, 25 are directed into an "upstanding" position so that they, by means of the pre-stressing, strive to rise up and support the tunnel walls 17', 18' even after a certain flattening, which may occur in a sales packaging. A highly resilient action is, however, achieved also in other transversal directions by the folding and the built-in elastic deformation resistance of the material.

The barrier may, due to its design, stop or slow down the liquid spreading enough for the liquid to have time to be absorbed by an underlying absorption body. The barrier may be more or less liquid-proof, by being made of a liquid-proof or hydrophobic material. The folding of the material and the thickness of the barrier also contribute to the liquid-stopping effect. It is, however, no disadvantage if the barrier is pervious to steam.

Figure 3:
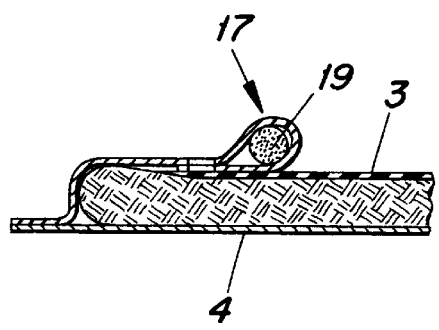
FIG. 3 is a broken cross-section corresponding to FIG. 2, but with elastic means in a second embodiment, FIG. 4 diagrammatically shows, in perspective view, an apparatus for the manufacture of an absorbent article according to the invention.

FIG. 3 shows the edge-leakage barrier 17 in a second embodiment, where the elastic means consists of a cord of for example foam material or fibre material, yielding a resilient action to the barriers in all directions, seen in a cross-section, i.e. a transversal elasticity. The cord may advantageously be pre-stretched, i.e. pre-stressed in the longitudinal direction, into a transversal dimension below the transversal dimension of the channel during manufacture, which after off-loading yields a dimensional increase in a transversal direction and thereby a mechanical locking against the tunnel wall and a pre-stressing in a transversal direction resulting in an increased resilient action.

Furthermore, the elastic means in both embodiments have both in common that they need not be fastened in the wall of the barrier, whereby unnecessary tensions are avoided.

Figure 4:
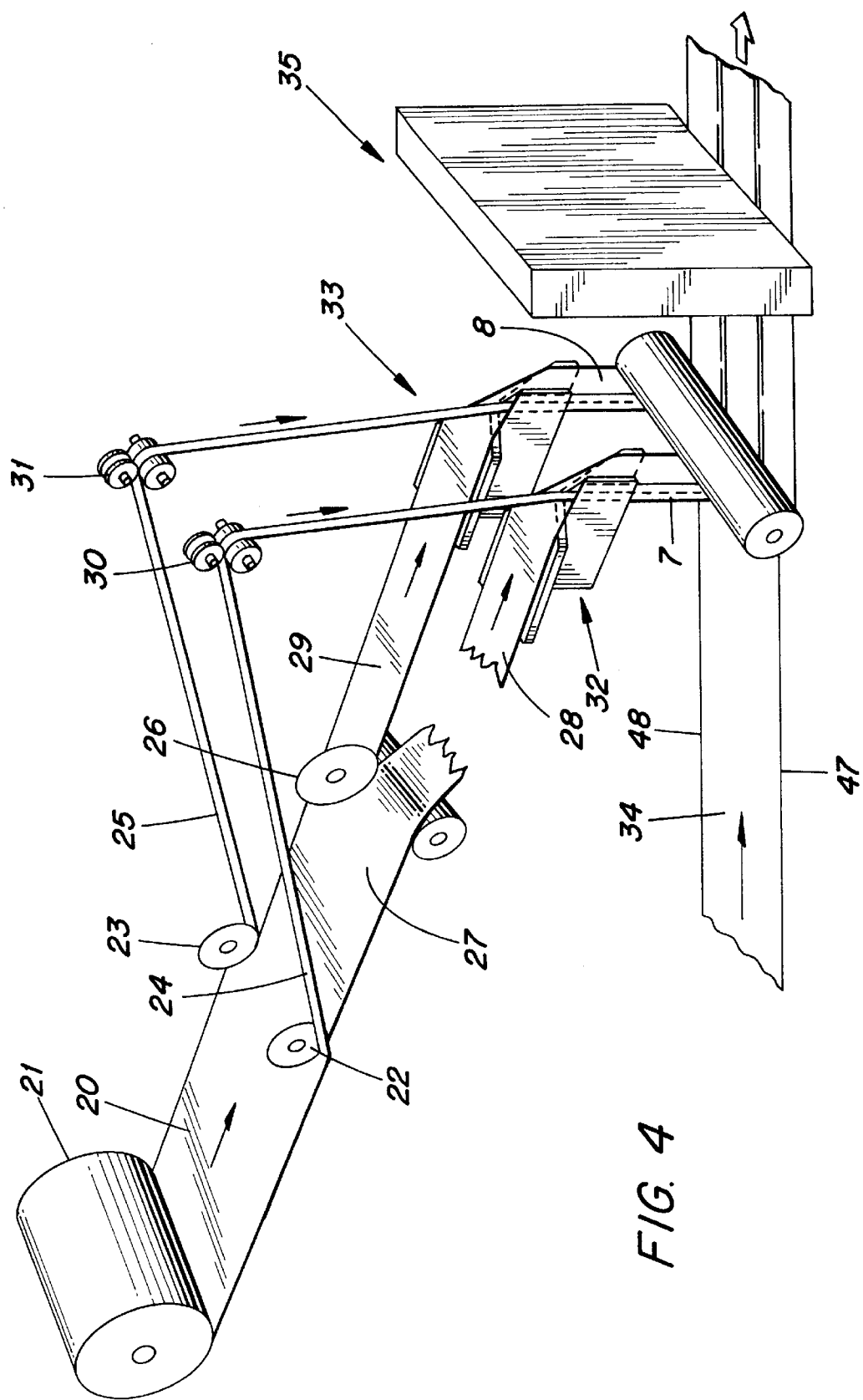

Referring to FIG. 4, a method and an apparatus will be described, for the manufacture of the liquid-absorbent article according to the invention. Hereby, the description is limited to the manufacture of the portion of the cover 2, which supports the edge-leakage barriers 17, 18. The rest, i.e. the manufacture of the absorption body, the liquid-proof sheet 4 and their joining together with the rest of the cover is known in the prior art and should not require a closer explanation.

The apparatus according to FIG. 4 starts off from one and the same material line 20, continually rolled off a storage roll 21. Outer edge-cutting cutter-rollers 22, 23 are included in the apparatus for cutting out two outer edge-strips 24, 25 in order to form the filling or the elastic means in the barriers. A centrally cutting cutter-roller 26 divides the interstitial material line 27 into two parts 28, 29 to form the edge-strips 7, 8 with the tunnel portions in the edge-leakage barriers 17, 18.

The outer edge-strips 24, 25 are each fed to their own folding device 30, 31 for folding the strips into a bellows-shaped cross-section, which will be described in greater detail below.

A fold-over device 32, 33 is also included in the apparatus for each part 28, 29 of the line, in which the barrier is formed by folding into a tunnel shape with the folded strip inserted, which will be described in greater detail below.

From a storage roll (not shown), a material line 34 is fed, which is to form the liquid-pervious cover-sheet 3. The completed edge-strips 7, 8 with associated barriers 17, 18 are fed spaced apart a distance adapted to the width of the material line 34, and joined together with the same and is brought through a joining device 35 for joining of the folded-over edge-strips 7, 8 with the longitudinal edges 47, 48 of the material line 34. The device 35, for example comprises a combined heating- and embossing device, utilizing ultra-sound.

Figure 5:
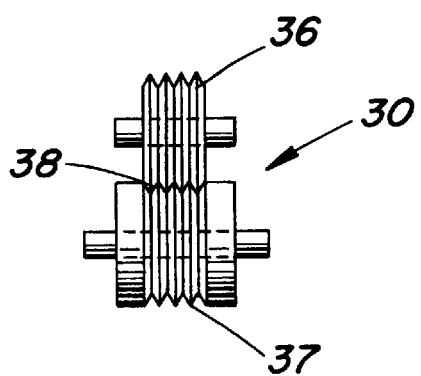
FIGS. 5 and 6 shows a folding device included in the invention.
Figure 6:
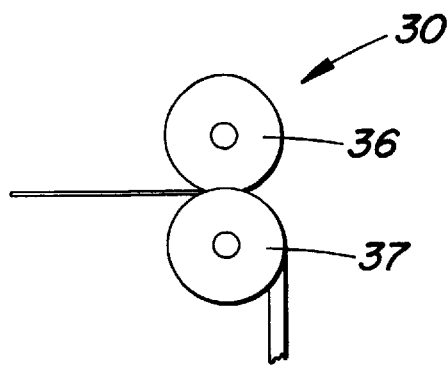

The folding devices 30, 31 in the shown embodiment, comprise, as is best seen in FIGS. 5 and 6, two rotating rollers 36, 37 having zig-zag-shaped tracks 38, engaging each other. When the strips 24, 25 are fed through these rollers they are given the same shape as the profile of the tracks, i.e. a zig-zag-shape or a bellows-shape, after which the strips are fed onto the fold-over devices 32, 33, see FIG. 7.

Figure 7:
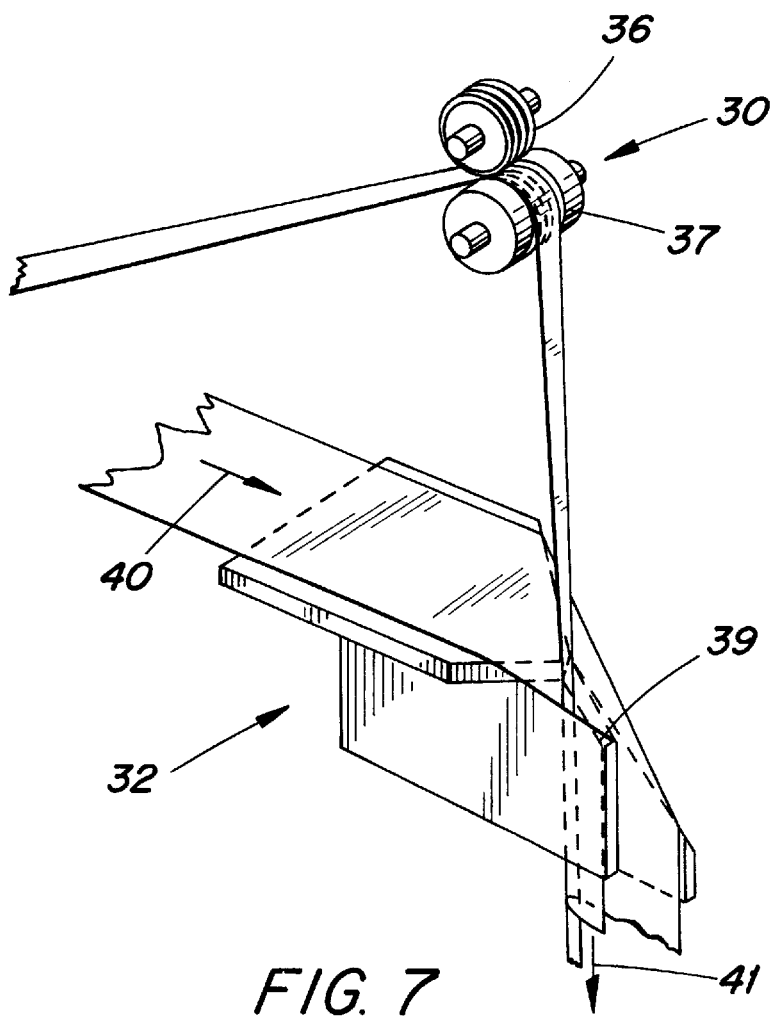
FIG. 7 shows a perspective view of the folding device and a fold-over device according to the invention.

The fold-over device 32, in the embodiment shown in FIGS. 7, 8 and 9, comprises a fold-plate arrangement whose main part consists of a gap-like longitudinal, outwardly open chute 39, extending substantially transversally (see the arrow 40) to the feeding direction 41. Furthermore, two redirection-edges 42, 43 situated asymmetrically in the horizontal plane (the in-feed plane) is included, whilst the inlet of the chute 39 displays two, relative to the horizontal plane oblique redirection-edges 44, 45.

By the edge-strip being drawn along the longitudinal direction of the chute 39, the folded-over portion of the edge-strip is formed. From FIG. 7, it is apparent that the strip 24, folded into a bellows-shape, is fed somewhat angled into the chute 39 from the folding device 30, whereby the strip is guided and compressed towards the bottom 46 of the chute. Hereby, it is assured that the tunnel is subsequently closed without the fill-in material being trapped between the sealed sheets.

The invention is not limited to the embodiments described above and illustrated in the appended drawings, but may be varied within the scope of the appended claims. For example, it is possible that the edge-leakage barriers are formed by folding of the cover-sheet 3 only. The strip 24, 30 25 may be twined instead of all in combination with folding. The folding may also extend in a transversal direction. The folded strips may be laid at an angle to the surface of the cover sheet i.e. turned 90°, or obliquely, for example with a 45° inclination. The barriers may extend differently, they may for example extend transversely along the longitudinal direction of the article or they may extend curve-shaped. The barriers may be included in other articles for hygiene protection, for example diapers, incontinence protection, whereby the barriers may be designed with considerably larger dimensions.

We claim:

1. A disposable liquid-absorbent article to be worn by a user said article comprising:
   a substantially longitudinal absorption body; and
   a cover enclosing the absorption body, the cover having a first side, facing the user in an in-use position, which displays a liquid pervious first cover-sheet and a second side, facing away from the user in an in use position, which displays a second cover sheet,
   wherein said first side is provided with at least one longitudinal liquid barrier means including a portion formed by a material layer folded into a tunnel shape such that said portion forms a channel with a longitudinal tunnel wall,
   wherein said portion folded into a tunnel-shape encloses longitudinal elastic means with an elastically resilient supporting action acting in all directions transverse to the longitudinal direction of the article against the tunnel wall of the folded portion:
   wherein said longitudinal elastic means in an unloaded condition displays a transversal dimension exceeding the transversal dimension of the channel but in and for mechanical locking longitudinally against the tunnel wall.

2. Article according to claim 1, wherein said longitudinal elastic means comprises a strip of material, folded along a longitudinal axis thereof.

3. Article according to claim 1, wherein said longitudinal elastic means consists of fibre cloth.

4. Article according to claim 1, wherein said longitudinal elastic means consists of an elastic strip of fibre- or foam material.

5. Article according to claim 2, further including two longitudinal edge-strips forming two edge-portions of the cover, wherein a longitudinal portion of said edge-strips forms said tunnel-shaped portion.

6. Method for the manufacture of a disposable liquid-absorbent article to be worn by a user, the article including a substantially longitudinal absorption body and a cover enclosing the same, the cover having a first side, facing the user in an in-use position, which is provided by a liquid-pervious first cover-sheet and a second side, facing away from the user in an in-use position, which is provided with a second cover-sheet, whereby on said first side is arranged at least one longitudinal liquid-barrier means, formed by folding a portion of material into a tunnel-shape, and thereby forming a longitudinally closed tunnel wall, said method comprising:
   holding the folded-over portion open;
   inserting longitudinal elastic means, said longitudinal elastic means being pre-stressed into a reduced transversal dimension into the folded-over portion,
   folding the folded portion and giving the folded portion said tunnel-shape enclosing said longitudinal elastic means, said longitudinal elastic means having, in an unload condition, a transversal dimension exceeding a transversal dimension of a channel formed by the longitudinal closed tunnel wall for mechanical locking longitudinally against the tunnel wall.

7. Method according to claim 6, wherein said longitudinal elastic means is formed by folding a strip of material.

8. Method according to claim 7, wherein said strip of material is formed by cutting off an outer edge-portion of said material.

9. Apparatus for the manufacture of a disposable article to be worn by a user, the article including a substantially longitudinal absorption body and a cover enclosing the same, the cover having a first side, facing the user in a in-use position, which is provided with a second cover-sheet and a second side, facing away from the user in a in-use position, which is provided with a second cover-sheet, said first side including at least one longitudinal liquid-barrier means, formed by folding a portion of a material line into a tunnel-shape, forms a longitudinal closed tunnel wall, said apparatus comprising:
   a fold-over device for forming said folded-over portion into an open fold;
   devices for continually feeding said longitudinal elastic means being prestressed into a reduced transversal dimension; and
   devices to seal the fold into a tunnel-shape.

10. Apparatus according to claim 9, further including a folding device for forming said longitudinal elastic means by longitudinally folding a strip of material.

11. Apparatus according to claim 9, wherein the folding device comprises a fold-plate arrangement with redirection-edges for redirection of the material line towards an inlet to a gap-shaped, open chute.

12. Apparatus according to claim 9, further comprising outer edge-cutting means for cutting out outer edge-strips from said material line said edge-strips thus forming said longitudinal means.

* * * * *

UNITED STATES PATENT AND TRADEMARK OFFICE
CERTIFICATE OF CORRECTION

PATENT NO.     : 6,066,121
DATED          : May 23, 2000
INVENTOR(S)    : Lindquist et al.

Page 1 of 1

It is certified that error appears in the above-identified patent and that said Letters Patent is hereby corrected as shown below:

Column 5,
Line 51, delete "but"

Column 6,
Line 18, after "means" insert --into the folded-over portion--;
Line 20, delete "into the folded-over portion" and after the comma insert --and--.
Line 24, change "unload" to --unloaded--.

Column 6,
Line 48, after "dimension" insert --, into the open fold; said longitudinal elastic means having, in an unloaded condition, a transversal dimesion exceeding dimension of a channel formed by the tunnel wall in and for mechanical locking longitudinally against the tunnel wall--.

Signed and Sealed this

Thirty-first Day of July, 2001

*Attest:*

*Attesting Officer*

NICHOLAS P. GODICI
*Acting Director of the United States Patent and Trademark Office*